United States Patent
Calderone

(10) Patent No.: US 9,144,702 B2
(45) Date of Patent: Sep. 29, 2015

(54) MUSCULAR EVALUATION AND EXERCISE DEVICE

(71) Applicant: Michael P. Calderone, Brighton, MI (US)

(72) Inventor: Michael P. Calderone, Brighton, MI (US)

( * ) Notice: Subject to any disclaimer, the term of this patent is extended or adjusted under 35 U.S.C. 154(b) by 183 days.

(21) Appl. No.: 13/788,557

(22) Filed: Mar. 7, 2013

(65) Prior Publication Data

US 2014/0256516 A1    Sep. 11, 2014

(51) Int. Cl.

| A63B 21/062 | (2006.01) |
|---|---|
| A63B 21/00 | (2006.01) |
| A63B 21/06 | (2006.01) |
| A63B 21/012 | (2006.01) |
| A63B 23/035 | (2006.01) |
| A63B 23/12 | (2006.01) |
| A61B 5/103 | (2006.01) |

(Continued)

(52) U.S. Cl.
CPC ............. *A63B 21/0615* (2013.01); *A61B 5/103* (2013.01); *A63B 21/0125* (2013.01); *A63B 23/03525* (2013.01); *A63B 23/1209* (2013.01); *A63B 23/1281* (2013.01); *A61B 5/224* (2013.01); *A61B 2505/09* (2013.01); *A63B 23/1236* (2013.01); *A63B 2021/0616* (2013.01); *A63B 2071/0072* (2013.01); *A63B 2071/025* (2013.01); *A63B 2220/13* (2013.01); *A63B 2220/16* (2013.01); *A63B 2220/17* (2013.01); *A63B 2220/24* (2013.01); *A63B 2220/52* (2013.01); *A63B 2230/01* (2013.01)

(58) Field of Classification Search
CPC ................... A63B 21/00032; A63B 21/00047; A63B 21/00061; A63B 21/00065; A63B 21/00069; A63B 21/00072; A63B 21/00181; A63B 21/012; A63B 21/0125; A63B 21/015; A63B 21/0615; A63B 21/0616; A63B 21/0617; A63B 21/062; A63B 21/08; A63B 21/1457; A63B 21/1465; A63B 21/1469; A63B 21/1492; A63B 21/1496; A63B 2021/0623; A63B 2021/0626; A63B 23/1209; A63B 23/1218; A63B 2208/0223; A63B 2208/0233
USPC .................. 482/98, 92–94, 97, 104, 110, 142
See application file for complete search history.

(56) References Cited

U.S. PATENT DOCUMENTS

| 3,285,070 A | 11/1966 | McDonough |
|---|---|---|
| 3,573,865 A | 4/1971 | Annas et al. |

(Continued)

OTHER PUBLICATIONS

Vic Sussman, Flexing Your Muscles Around the House, U.S News & World Report, May 10, 1993, pp. 77-79, vol. 114, No. 18, Washington D.C., U.S.A.

*Primary Examiner* — Loan H Thanh
*Assistant Examiner* — Megan Anderson
(74) *Attorney, Agent, or Firm* — J. Gordon Lewis

(57) ABSTRACT

An apparatus for the development of upper body parts and muscles is disclosed. The apparatus includes a base on which is mounted a seat supported above the base and a forearm pad disposed forward of the seat and supported above the base. A pivoted lever is pivoted at a first end to a seat support, a second end of the lever extends past the forearm pad a distance and includes a weight supporting pin which extends vertically upward. A lifting device is selectively and pivotally attached to the pivoted lever forward of the forearm rest. A plurality of weights are selectively attached to the weight support pin to vary the amount of force required to use the lifting device and raise the weights. A variety of attachments are selectively affixed to the lifting device to exercise various body parts and muscles.

20 Claims, 4 Drawing Sheets

(51) Int. Cl.
*A63B 71/00* (2006.01)
*A63B 71/02* (2006.01)
*A61B 5/22* (2006.01)

(56) References Cited

U.S. PATENT DOCUMENTS

| | | | |
|---|---|---|---|
| 3,858,873 A | 1/1975 | Jones | |
| 4,266,766 A | 5/1981 | Calderone | |
| 4,923,195 A | 5/1990 | Calderone | |
| D347,041 S | 5/1994 | Calderone | |
| 5,358,462 A | 10/1994 | Calderone | |
| 7,278,958 B2 * | 10/2007 | Morgan | 482/97 |
| 7,846,077 B2 * | 12/2010 | Osbak | 482/115 |
| 2007/0021280 A1 * | 1/2007 | Tyree | 482/94 |
| 2014/0100091 A1 * | 4/2014 | Ho et al. | 482/142 |

* cited by examiner

MUSCULAR EVALUATION AND EXERCISE DEVICE

TECHNICAL FIELD

The present invention relates to the field of exercise devices, and more particularly the present invention relates to the field of exercise devices for developing targeted body parts and muscles. Even more particularly, the present invention relates to the field of exercise devices for medical application for objectively measuring the state of development of muscles of the shoulders, upper arms, forearms, wrists and back.

BACKGROUND OF THE INVENTION

A search of issued U.S. patents in the field of muscular exercising devices and apparatus reveals U.S. patents related generally to the field of the present invention but which do not anticipate nor disclose the device of the present invention. The discovered U.S. patents relating to the present invention are discussed herein below.

U.S. Pat. No. 3,573,865 to Annas et al. entitled "Weight Shifting Mechanism for Exercising" discloses an exercise device wherein the user pushes against an arcuately movable pedal which is connected through a mechanism to pivot a weighted beam about a fixed fulcrum. A seat is provided against which the user of the device rests while employing the device. This device employs cables and pulleys in its operation.

U.S. Pat. No. 3,858,873 to Jones entitled "Weight Lifting Exercising Devices" discloses an apparatus for development of body parts. The apparatus includes a frame on which is mounted a force applying member against which the user exerts a force for developing body parts and muscles. The device employs a seat for supporting the user, and a system of cables and pulleys is employed to exert force against the force applying member. The force exerted is continuously varied over the full range of rotation of the force applying member.

U.S. Pat. No. 3,285,070 to McDonough entitled "Muscular Evaluation and Exercising Apparatus" discloses an exercise apparatus employing a hinged weighted arm affixed to one end of a table or support. Resistance against motion is provided by a clutch which is adjustable to vary the amount of resistance imposed.

None of the above listed U.S. patents disclose nor anticipate an exercise device comprising a base with a seat supported above the base, a forearm pad disposed forward of the seat and supported above the base, a pivoted lever pivoted at a first end to a seat support and including a second end extending past the forearm pad a distance, a weight supporting pin extending vertically upward from the lever second end, an attachment post pivotally attached to the pivoted lever forward of the forearm rest, a lifting means selectively attached to the lifting post, and a plurality of weights selectively attached to the weight support pin to vary the amount of force required to raise the lifting means.

U.S. Pat. No. 4,266,766 to Calderone entitled "Exercise Device" discloses an apparatus for the development of upper body parts and muscles. The apparatus includes a base on which is mounted a seat supported above the base and a forearm pad disposed forward of the seat and supported above the base. A pivoted lever is pivoted at a first end to a seat support, a second end of the lever extends past the forearm pad a distance and includes a weight supporting pin which extends vertically upward. A lifting device is selectively and pivotally attached to the pivoted lever forward of the forearm rest. A plurality of weights are selectively attached to the weight support pin to vary the amount of force required to use the lifting device and raise the weights. A variety of attachments are selectively affixed to the lifting device to exercise various body parts and muscles.

U.S. Pat. No. 4,923,195 to Calderone entitled "Exercise Device" discloses an apparatus for the development of upper body parts and muscles. The apparatus includes a base on which is mounted a seat supported above the base with an adjustable forearm pad which is adjustably disposed forward of the seat and supported above the base by an adjustable forearm pad support. A pivoted lever is pivoted at a first end adjacent the seat, a second end of the lever extends past the forearm pad a distance and includes a weight supporting pin which extends vertically upward. A lifting device is selectively and pivotally attached to the pivoted lever, including mechanisms for adjusting the height and the forward or rearward position of the lifting device along the pivoted lever. A plurality of weights are selectively attached to the weight support pin to vary the amount of force required to use the lifting device and raise the weights. A variety of attachments are selectively affixed to the pivoted lever to exercise various body parts and muscles.

U.S. Pat. No. 5,358,462 to Calderone entitled "Exercise Apparatus" discloses an arrangement wherein two attachments are provided for an exercise apparatus of the type having a lever arm with an end pivotally connected to a base and a free end adapted to receive weights. A tower attachment provides a flexible tensile member connected at an end of the lever arm, with intermediate portions borne across elevated pulleys, and connectable at another end to various handles, by which a user can perform various pull-down and rowing exercises. A shoulder bar attachment has an elongated body connected at one end to the lever arm and having another end which accommodates the user's head and shoulders and which is provided with handles, allowing a user to perform various press and leg raise exercises.

U.S. Design Pat. No. D347,041 to Calderone entitled "Handle Assembly for a Physical Exerciser" describes an ornamental design for a handle assembly for a physical exerciser, such as the physical exercise apparatus described in U.S. Pat. No. 5,358,462.

U.S. Pat. Nos. 4,266,766, 4,923,195, 5,358,462 and D347,041 described herein are commonly owned, with the present application, by Michael P. Calderone. The specifications, drawings, abstracts and claims of U.S. Pat. Nos. 4,266,766, 4,923,195, 5,358,462 and D347,041 are incorporated herein by reference to include their respective teachings.

The aforesaid apparatus are typically intended for and can be advantageously applied in traditional home and commercial gym settings wherein the intended user is in average or superior physical condition. They can be, however, of limited value in situations wherein the user is infirm, suffers from severe or chronic injuries, physical limitations, or is undertaking a medically supervised course of physical therapy. It therefore has long been desired to provide exercise devices suitable for developing or restoring targeted body parts and muscles as part of a medical or physical therapy regimen.

SUMMARY OF THE INVENTION

It is an object of the present invention to provide an exercise device for exercising and developing specifically targeted body parts and muscles.

It is also an object of the present invention to provide a device for exercising upper body parts and muscles wherein the force required to operate the device can be varied by varying the amount of weight attached to the device.

It is another object of the present invention to provide an exercise device including a user manipulated counterbalanced elongate beam which enables independent variation of the degree beam imbalance about a center pivot by placement of free weights at each end of the beam, and independent variation of the overall mass of the beam by varying the aggregate number of free weights.

According to the preferred embodiment of the invention, the exercise device for therapeutic development of targeted user musculature include a base, a seat supported above the base by a vertically extending structure, a forearm pad adjustably disposed forward of the seat and supported above the base by an adjustable forearm pad support, an adjustably counterbalanced elongate beam assembly having a fore end portion extending forwardly of said seat, an aft end portion extending rearwardly of said seat, and a pivot interconnecting said beam assembly to said vertical seat structure while enabling rotational freedom of said beam assembly between first and second limits of travel, and lifting means pivotally attached to the fore end portion forward of said forearm pad.

According to another aspect of the invention, a second, infinitely adjustable weight assembly is carried on one or both end portions of the beam assembly. This arrangement enables precise selection of the beam's weight imbalance.

According to another aspect of the invention, the adjustable weight assembly includes an elongated guide member extending generally parallel to an axis of said elongate beam and a dedicated weight carried with said guide member for incremental axial adjustment there-along, and wherein said free weight support pin and said adjustable weight assembly are generally axially equidistant from said pivot.

According to another aspect of the invention, the free weights are incrementally sized between a minimum weight of X Kg. and a maximum weight of Y Kg., wherein said dedicated weight weighs approximately 0.5X Kg.

According to another aspect of the invention, a dynamic tension device operative to resist rotational displacement of said counterbalanced beam assembly between said limits of travel. The dynamic tension device includes a fixed caliper operable to selectively engage opposed lateral surfaces of said counterbalanced beam assembly, According to another aspect of the invention, the aft end portion of the elongate beam forms a semi-circular member depending from said fore end portion adjacent said pivot, wherein the semi-circular member has a substantially constant radius coaxially centered with said pivot. The semi-circular member extends rearwardly through a registering slot formed in said seat support structure, and carries a semi-circular scale registering with a fixed indicator carried by said seat support structure to provide an angular position indication to an attendant clinician.

According to another aspect of the invention, the semi-circular member carries an intermediate stop operative selectively vary the first and/or second limit of travel.

These and other features and advantages of this invention will become apparent upon reading the following specification, which, along with the drawings, describes preferred and alternative embodiments of the invention in detail.

BRIEF DESCRIPTION OF THE DRAWINGS

The present invention will now be described, by way of example, with reference to the accompanying drawings, in which:

FIG. 3a, is a cross-sectional view, on a further enlarged scale, taken on lines 3a-3a of FIG. 3;

FIG. 5, is a top plan view of the seat employed in the muscular evaluation and exercise device of FIG. 1.

Although the drawings represent embodiments of the present invention, the drawings are not necessarily to scale and certain features may be exaggerated in order to illustrate and explain the present invention. The exemplification set forth herein illustrates an embodiment of the invention, in one form, and such exemplifications are not to be construed as limiting the scope of the invention in any manner.

DESCRIPTION OF THE PREFERRED EMBODIMENT

Figure 1:
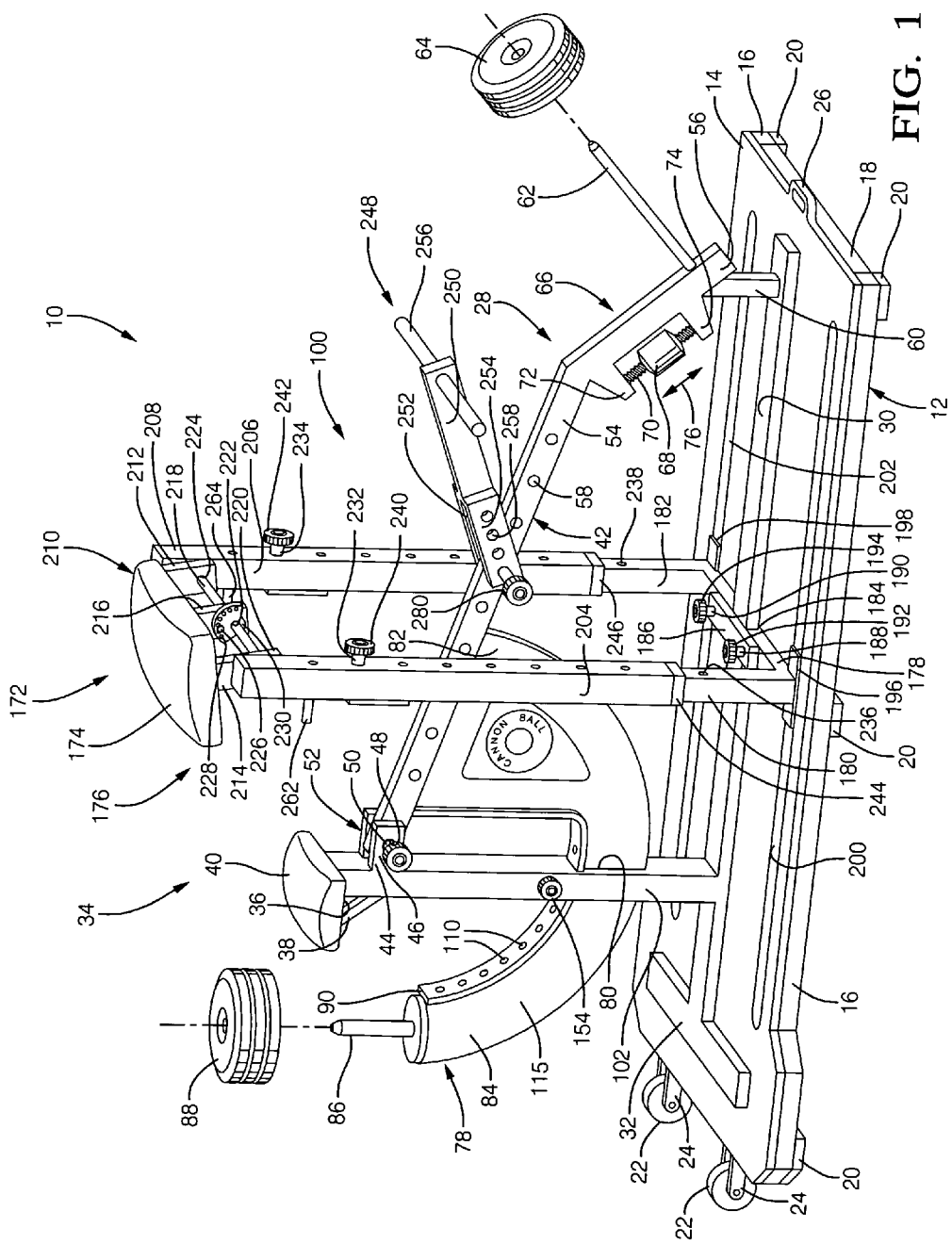
FIG. 1, is a perspective view of a muscular evaluation and exercise device embodying the present invention.

Referring to FIG. 1, a preferred embodiment of a muscular evaluation and exercise device 10 is illustrated. The exercise device 10 comprises a base assembly 12 of welded construction including a generally rectangular base plate 14, two longitudinally extending side members 16 and two laterally extending end members 18. The side and end members 16 and 18, respectively, serve to rigidify the base plate 14 and to elevate the base plate 14 above the floor (not illustrated) upon which it rests in application. The side and end members 16 and 18, respectively, are dimensioned and arranged to frame the perimeter of the base plate 14. The base plate 14 is preferably formed from slip-resistant material such as diamond steel plate. The side and end members 16 and 18, respectively, are preferably formed from square section steel tube.

In use, the exercise device 10 rests on a flat floor surface, and is prevented from inadvertent sliding movement thereon by resilient pads 20 mounted on the lowermost surfaces of the side and end members 16 and 18, respectively, to dampen vibration and momentary shock loads, and to adapt for minor irregularities in the floor surface. Relocation of the exercise device 10 is achieved by a pair of laterally spaced caster wheels 22 mounted to associated longitudinal frame extensions 24 affixed to one of the end members 18. A hand grip member 26 is affixed to the opposed end member 18. Relocation of the exercise device 10 is accomplished by grasping the hand grip member 26, pivotally raising the exercise device 10 about the rolling axis of the caster wheels 22, and manually relocation the exercise device 10 in dolly-fashion to a new location. Pivotally raising the exercise device 10 momentarily lifts and disengages the resilient pads 20 from the floor.

An exercise device assembly 28 is rigidly affixed upon the upper surface of the base assembly 12. The exercise device assembly 28 includes a longitudinally extending member 30 terminating at a rear or aft end thereof adjacent a laterally extending cross-member 32. Longitudinally extending member 30 is permanently joined at the midpoint of laterally extending cross-member 32 such as by welding. The generally "T" configured longitudinally extending member 30 and laterally extending cross-member 32 are then rigidly affixed to the base plate 14 by bolts, weldments or the like.

A seat support structure 34 composed of square section steel tube is attached to the longitudinally extending member 30 at a location spaced forward of the laterally extending cross-member 32, and extends vertically upward therefrom. The seat support structure 34 is affixed to the longitudinally extending member 30 by welding, fasteners, or other suitable means. A pad support 36 comprising a rigid planar member deployed in a horizontal plane is affixed atop the seat support structure 34 by welding or other suitable means. A bracket 38 extends at an angle between the pad support 36 and the seat support structure 34 to add stability to the pad support 36. A padded seat 40 overlays the pad support 36 to render comfort to a person sitting thereon.

The exercise device assembly 28 includes a rigid elongate beam 42 disposed in a laterally centered orientation above the longitudinally extending member 30. The elongate beam 42 is preferably formed of tubular steel having a nominal rectangular cross-section. The rearmost end of the elongate beam 42 is pivotally interconnected to an upper portion of the seat support structure 34 for limited rotation with respect thereto. A "U" shaped bracket 44, forming a laterally opposed pair of legs 46 is permanently affixed to the upper portion of the seat support structure 34 by welding or other suitable means proximate the pad support 36, with the legs 46 extending in the forward direction. A pair of aligned apertures 48 pass transversely through the legs 46 of the "U" shaped bracket 44. A laterally transverse aperture (not illustrated) is formed in the elongated beam 42 adjacent the rear end thereof. In assembly, the elongate beam aperture is concentrically aligned with the bracket apertures 48. A pivot pin 50 is interference fit within bracket apertures 48 and slidingly extends through the intermediate beam transverse aperture to permit limited free relative rotation there between. This structure is collectively deemed a pivot assembly 52. If a more robust structure is desired, such as for medical therapeutic applications, appropriate bushings or bearings (sleeve or roller type) can be applied in the pivot assembly 52 without departing from the scope of the present invention.

The elongate beam 42 extends forwardly from the pivot assembly 52 defining a "hockey stick" shape including an elongate "handle" portion 54 terminating in a "blade" portion 56. A plurality of axially spaced, transversely extending apertures 58 are formed in the "handle" portion 54 of the elongate beam 42. The "blade" portion 56 extends forwardly and downwardly at an acute offset angle from the axis of the "handle" portion 54. A pivot stop 60 extends vertically upwardly from the forward end of the longitudinally extending member 30 to support the forward most end of the "blade" portion 56 and define a first or down stop for the elongate beam 42. A weight support pin 62, preferably formed of 1 inch diameter steel bar stock, is affixed to the "blade" portion 56 and extends generally upwardly (at all possible angular orientations of the elongated beam 42) to selectively support one or more free weights or barbell plates 64. A central aperture of each free weight 64 is slid over the pin 62 to retain the weights 64 in their illustrated positions. As illustrated in FIG. 1, the elongated beam 42 is in a first or lowermost limit of rotational travel. The elongated beam 42 second or upper-most limit of travel (not illustrated) is approximately 90 degrees counter-clockwise from the orientation illustrated in FIG. 1.

An infinitely adjustable weight assembly 66 is carried with the elongated beam 42, and preferably with the "blade" portion 56 thereof. The adjustable weight assembly 66 consists of a tubular weight 68 threadably carried with an elongated threaded shaft 70 fixedly supported at both ends thereof by extensions 72 and 74 integrally formed with and depend from the "blade" portion 56. The threaded shaft 70 is preferably disposed with its axis of elongation arranged parallel with and offset from the axis of elongation of the "blade" portion 56. The weight 68 can be manually adjusted to effect fine, incremental bidirectional adjustment along the axis defined by the threaded shaft 70 as indicated by arrow 76. Thus, the infinitely adjustable weight assembly 66 provides a finely controllable balance adjustment feature wherein the moment arm (fixed weight×variable distance) is variable.

Figure 3:
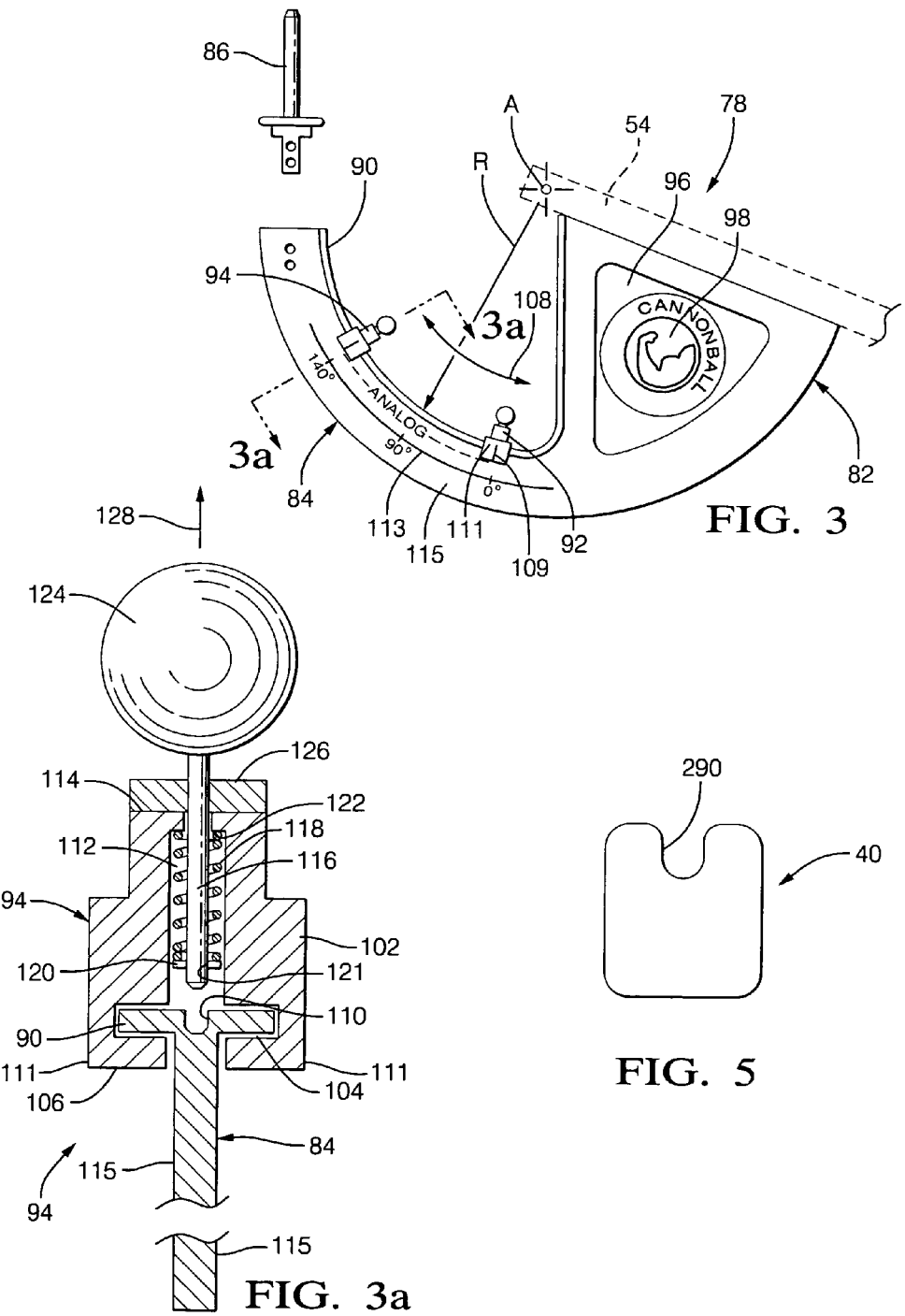
FIG. 3, is an exploded plan view, on an enlarged scale, of the aft end portion of a counterbalanced elongate beam employed in the muscular evaluation and exercise device of FIG. 1.

Referring to FIGS. 1 and 3, a generally arcuately shaped counterweight beam assembly 78 is rigidly affixed to the end of the elongate beam 42 adjacent the pivot assembly 52 and extends rearwardly therefrom through a "T" shaped longitudinal opening 80 formed in the seat support structure 34. The counterweight beam assembly 78 is preferably formed of heavy gauge steel having a base or root portion 82 affixed to a lower surface of the elongate beam 42 such as by welding, and a rearwardly directed arcuate aft portion 84 extending through and rearwardly beyond the seat support structure 34. The arcuate aft portion 84 is formed in a substantially fixed radius, designated by arrow R, about the axis of rotation A defined by the pivot assembly 52, and extends through an approximately 90 degree sector.

The rearward most cantilevered part of the arcuate end portion 84 supports a rear weight support pin 86 which extends upwardly therefrom in all possible relative angular positions of the combined elongate beam 42 and counterweight rear beam assembly 78, thereby ensuring retention of counterbalancing free weights or barbell plates 88 carried thereby. As best illustrated in FIG. 3a, the upper surface of the arcuate end portion 84 defines a laterally enlarged "T" shaped flange 90 extending there along. In addition to providing rigidity to the cantilevered portion of the arcuate end portion 84, the "T" shaped flange 90 defines a guideway for an adjustable supplemental down stop 92 and an up stop 94. A generally triangularly shaped central area 96 is formed in the base portion 82 of the counterweight beam assembly 78 to reduce weight while maintaining rigidity. Advertising or instructional indicia 98 is affixed within the recessed triangular central area 96.

Definitionally, the elongate beam 42, the weight support pin 62, the infinitely adjustable weight assembly 66, the counterweight beam assembly 78, the supplemental down stop 92, the up stop 94 and the rear weight support pin 86, as well as free weights 64 and 88 carried on the support pins 62 and 86, respectively, are deemed to constitute an "adjustably counterbalanced elongate beam assembly" 100. In application, all of the components comprising the adjustably counterbalanced elongate beam assembly 96 rotate in unison about the axis defined by the pivot assembly 52 through a range of motion delimited in the clockwise sense by either the pivot stop 60 or the supplemental down stop 92, and in the counter-clockwise sense by the up stop 94.

The adjustably counterbalanced elongate beam assembly 100 is configured, weighted and dimensioned to ensure that the product of the aggregate center of mass all of the elements thereof forward of the axis of rotation of the pivot assembly 52 (defined as CMf) times the longitudinal distance there between (defined as Df) equals or exceeds the product of the aggregate center of mass all of the elements thereof rearward of the axis of rotation of the pivot assembly 52 (defined as CMr) times the longitudinal distance there between (defined as Dr). Restated, the two opposed moment arms are nearly equal. This relationship can be described as:

$$CMf \times Df \cong CMr \times Dr$$

The forgoing relationship is varied by selectively placing differing amounts of free weights on the front and rear weight support pins 62 and 86, respectively. Free weights are typically sized incrementally in steps, such as 2½ lbs., 5 lbs., 10 lbs., 20 lbs., 50 lbs., and the like. The degree of weight imbalance between the front and rear moment arms of the beam assembly 100 is substantially determined by the offsetting aggregate stack-up of weights at the front and rear support pins 62 and 86, respectively. In therapeutic applications, it often desirable to reduce the imbalance to an amount less than the smallest free weight (ex. 2½ lbs.). In the present invention, the dedicated weight 68 is precisely repositionable in increments effecting a substantially smaller than 2½ lbs. adjustments. Given the potential axial displacement of the tubular weight 68 along the adjustment shaft 70, the applicant believes that a tubular weight of less than 1 lb. can provide the desired adjustability.

Referring to FIGS. 3 and 3a, the structural details and functionality of the supplemental down stop 92 and up stop 94 are illustrated in application with the counterweight beam assembly 78. FIG. 3a illustrates the up stop 94 which is functionally and structurally similar to the supplemental down stop 92. The up stop 94 has a rigid base member 102 having a longitudinally extending "T" shaped passage 104 opening through the bottom 106 thereof. The "T" shaped through passage 104 is dimensioned to slidingly engage the flange 90 of the arcuate portion 84 of the counterweight beam assembly 78 to enable selective positioning thereof as indicated by arrow 108. The flange 90 has a plurality of longitudinally aligned spaced through holes 110 formed therein. When locked into position, the base member 102 of each stop 92 and 94 serves as an abutment surface against the exposed outer surface of the seat support structure 34 to establish a limit of travel of the elongate beam assembly 100. An indicator line 109 is positioned on the lateral exterior surfaces 111 of the base members 102 of each down stop 92, 94, which registers with a range of motion indicator scale 113 positioned on the lateral exterior surfaces 115 of the arcuate aft portion 84 of the counterweight beam assembly 78 to provide a visual indication of the stop settings vis-à-vis the associated angular position of the beam assembly 100 at its selected end limits of travel.

The base member 102 has a through passage 112 communicating the top surface 114 of the member 102 with the "T" shaped passage 104. A plunger pin 116 extends through the passage 112. A compression spring 118 is disposed concentrically with the plunger pin 116 to continuously simultaneously bear downwardly on a flange member 120 carried with the plunger pin 116 and upwardly against a fixed step 122 formed in the through passage 112. The flange member 120 is fixedly disposed within a radially outwardly opening annular groove 121 formed within the lower end portion of the plunger pin 116. Thus, the plunger pin 116 is continuously urged downwardly and, when aligned with one of said through holes 110 will self engage with the flange 90. The opposed end of the plunger pin 116 extends upwardly above the top surface 114 of the base member 102, and is affixed to a manually operable control knob 124. A resilient pad 126 is disposed on the top surface 114 to provide cushioned support of the control knob 124. The stops 92 and 94 are repositioned simply by grasping the control knob 124 and pulling it upwardly as indicated by arrow 128. Thereafter, the stop 92, 94 is manually repositioned along the flange 90 until assuming a new desired position wherein the plunger pin 116 registers with the new desired flange through hole 110. Finally, the knob 124 is released, and the compression spring 118 forces the plunger pin 116 into the newly selected flange through hole 110.

Figure 6:
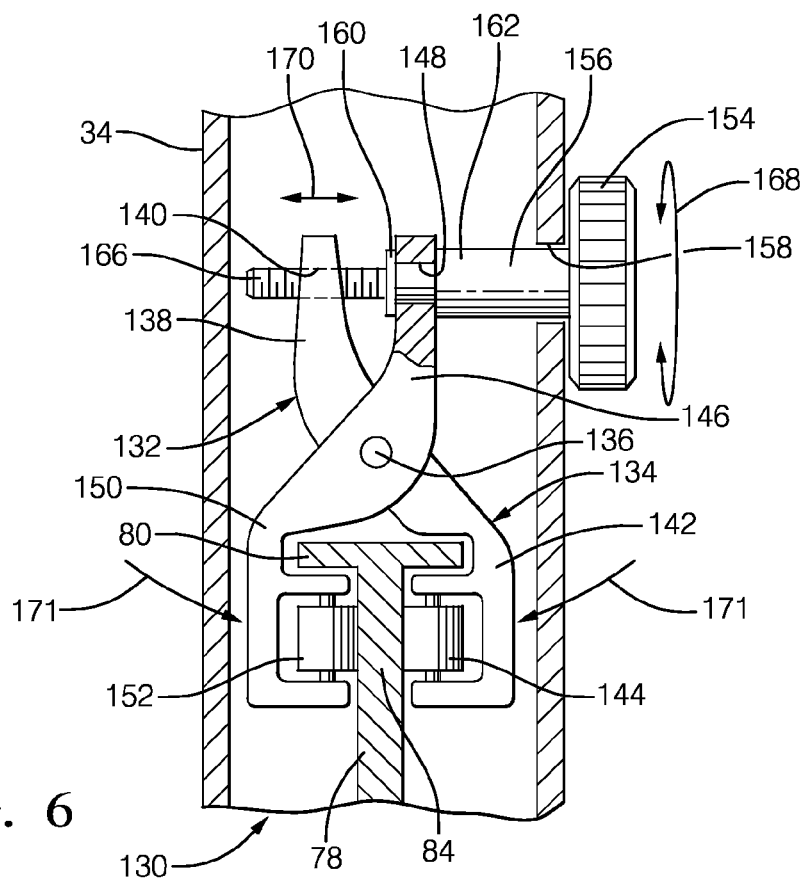
FIG. 6, is a plan view, on an enlarged scale, of the tensioner mechanism employed within the seat vertically extending structure of the muscular evaluation and exercise device of FIG. 1, as viewed longitudinally from the rear, the tensioner mechanism including adjustable rollers operative to control speed and smooth transition of motion/movement of the counterbalanced elongate beam.

Inertial characteristics of the adjustable counterbalanced elongate beam assembly 100 can be selected by staged offsetting loading of the fore and aft end portions while maintaining a fixed balance condition. Referring to FIG. 6, a dynamic tension device 130 can also be added to resist patient induced movement and acceleration of an otherwise counterbalanced elongate beam assembly 100.

The dynamic tension device 130 comprises a scissors-like apparatus including first and second substantially mirror image elongated levers 132 and 134, respectively, pivotally joined for relative rotation about an axle 136. Lever 132 has an upper leg portion 138 defining a laterally oriented threaded through bore 140 and a lower leg portion 142 carrying a resilient roller 144 for relative rotation. Similarly, lever 134 has an upper leg portion 146 defining a laterally oriented smooth walled through bore 148 and a lower leg portion 150 carrying a resilient roller 1152 for relative rotation.

The dynamic tension device 130 is preferably located within the seat support structure 34 adjacent the longitudinal opening 80 and the "T" shaped flange 90 of the arcuate aft portion 84 of the counterweight beam assembly 78 extending there through. The rollers 144 and 152 cooperatively face one another with the arcuate aft portion 84 of the counterweight beam assembly 78 passing there between (into and out of the plane of the drawing sheet carrying FIG. 6). An operator control knob 154 mounted externally of the seat support structure 34 is affixed with a control shaft 156 extending inwardly through an opening 158. The control shaft 156 defines left and right axially spaced apart annular flanges 160 and 162, respectively, and a reduced diameter intermediate bearing surface 164. The through bore 148 of the upper leg portion 146 is captured between the annular flanges 160 and 162. Thus, the control shaft 156 is free to rotate relative to the upper leg portion 146 but is axially fixed with respect thereto. The control shaft 156 also defines a threaded end portion 166 which, in assembly, is threadably engaged within threaded through bore 140.

The dynamic tension device 130 is operated by manual rotation of the operator control knob 154 as illustrated by arrow 168. Insodoing, the control shaft 156 rotates within through bore 148 maintaining their relative axial juxtaposition. Simultaneously, threaded shaft portion 166 rotates within threaded bore 140, thereby axially displacing the upper leg portion 138 leftwardly or rightwardly, as illustrated by arrow 170 as a function of the direction of rotation of the control knob 154. This translates into a pinching motion illustrated by arrows 171. When the tension device 130 is disengaged, the rollers 144 and 152 are spaced from the side walls of the arcuate aft portion 84 of the counterweight beam assembly 78. When the tension device 130 is engaged, the rollers 144 and 152 are increasingly drawn into engagement with the side walls of the arcuate aft portion 84 of the counterweight beam assembly 78 as illustrated by arrows 170. The increased engagement creates increased rolling friction, thereby smoothing transition of movement/motion and introducing a small amount of resistance of patient induced displacement of the entire counterbalanced elongate beam assembly 100.

Referring to FIG. 1, the muscular evaluation and exercise device 10 includes an adjustable forearm rest mechanism 172 supported on the base assembly 12. A forearm pad 174 is adjustably disposed forward of the seat 40 and is supported above the longitudinal member 30 by an adjustable forearm pad support mechanism generally designated 176. The adjustable forearm pad support mechanism 176 includes a second laterally extending cross member 178 arranged transversely to the longitudinal member 30 beneath the forearm pad 174 and a pair of opposed vertical supports 180, 182 extending upward from the ends of the second cross member 178 to the forearm pad 174. The adjustable forearm pad support mechanism 176 is also of welded construction made from square cross-section tubing. The second cross member 178 has disposed in its center upward surface a notch 184 adapted to receive longitudinal member 30. A pair of threaded apertures (not illustrated) are located adjacent each side of the notch 184. The adjustable forearm pad support 11 further comprises a flat, plate-like member 186, with a pair of apertures 188, 190 formed therein and configured to be aligned with the pair of threaded apertures in the cross member 178. A pair of large-headed hand adjustment knobs 192, 194 are provided to clampingly secure member 186 to the cross member 178. In use, the second cross member 178 is placed under and at right angles to the longitudinal member 30 in such a manner that longitudinal member 30 is received by the notch 184. The plate-like member 186 is placed on top of and parallel to second cross member 178, the assembly thereof containing longitudinal member 30. The threaded apertures (not shown) located proximate each side of notch 184 are aligned with apertures 188, 190 formed in the plate-like member 186, and threaded fasteners 192, 194 are threaded through apertures 188, 190 and threadably engaged with the threaded apertures. The position of the forearm pad 174 along the axis of longitudinal member 30 is adjusted to a selected position forward or rearward. Threaded fasteners 192 and 194 are turned by hand until plate-like member 186 is forced down against second cross member 178 so to fix forearm pad support 176 to longitudinal member 30 at the selected position to define a means for adjusting the longitudinal position of the forearm pad.

The lowermost portions of the vertical supports 180, 182 form longitudinally elongated guide flanges 196 and 198, respectively, disposed for sliding engagement with the upper surface of the base plate 14 whenever the forearm pad support mechanism 176 is repositioned. The guide flanges 196 and 198 serve to limit front to rear rocking of the forearm pad support mechanism 176 when subjected to patient loading. Furthermore, the lowermost portions of the vertical supports 180, 182 form longitudinally elongated guide members (not illustrated) extending downwardly therefrom into longitudinally oriented guideway slots 200 and 202. The guide members ride in the guideway slots 200 and 202 to limit the range of longitudinal adjustability of the forearm pad support mechanism 176, and prevent patient induced lateral displacement or rotation (when viewed from above).

A pair of opposed vertical sleeves 204 and 206 are telescopingly engaged over the vertical supports 180 and 182, respectively, and a forearm pad support tube 208 disposed in a horizontal plane extends between the opposed vertical sleeves 204 and 206 and is joined thereto by welding or other suitable means. Attached to the undersurface of the forearm pad 174 is a bracket 210 comprising a flat cross-piece 212 and a plurality of arms 214, 216 and 218 extending perpendicularly therefrom. Arms 214, 216 and 218 each have an aperture 220, 222 and 224 formed therein proximate the end opposite the flat cross piece 212. Apertures 220, 222 and 224 are adapted to slidingly engage forearm pad support tube 208. A lock pin 226 is supported from the cross piece 212. The lock pin 226 passes through an aperture in arm 216 and engages one of the apertures 228 in a plate 230 fixed to support tube 208 to selectively fix the forearm pad 174 to the forearm pad support tube 208 at a pre-selected position to define a means for adjusting the radial position of the forearm pad 174. The vertical sleeves 204 and 206 are formed of steel tube with nylon liners to provide smooth telescoping movement in cooperation with vertical supports 180 and 182.

A pair of aligned apertures 232 and 234 pass transversely through the vertical sleeves 204 and 206, respectively, and are manually aligned with a pair of mating apertures 236 and 238 selected from a plurality of spaced aligned apertures 236 and 238 which pass transversely through the pair of opposed vertical supports 180 and 182, respectively. A pair of quick-release, self-engaging pins 240 and 242 slidingly engage the aligned apertures 232 and 234 as well as 236 and 238, respectively, to selectively position the forearm pad 174 at a desired height and define a means for adjusting the height of the forearm pad 174. Resilient bumper stops 244 and 246 are provided on the bottom surface of the sleeves 204 and 206 to mitigate shock loading whenever the sleeves 204 and 206 are displaced to their lowest position and contact their respective guide flanges 196 and 198, respectively.

Lifting means, in the form of a lever assembly 248, is pivotally attached to said adjustability counterbalanced elongate beam assembly 100 in a mounting position forward of said forearm pad 174 and extending upwardly from said beam assembly 100. The lever assembly 248 comprises an elongate beam 250 which is bifurcated at one end to form two elongated, parallel flanges 252 and 254 which, in application, straddle the elongate beam assembly 100. A longitudinally elongated handlebar assembly 256 is affixed to an opposite end of the elongate beam 250. A plurality of axially spaced apart pairs of aligned apertures 258 are formed in flanges 252 and 254. The bifurcated end portion of the lever assembly 248 is selectively affixed to the beam assembly 100 by a quick release pin 260 extending through a pair of apertures 258 and an aperture 58 in the elongate beam assembly 100. Selecting different aperture pairs 258 in the flanges 252 and 254 varies the effective length of the lever assembly 248. Selecting different apertures 58 in the elongate beam assembly 100 varies the longitudinal positioning of the lever assembly 248.

Quick release pins 240, 242 and 260 are preferably of the push-pull or positive locking types. Push-pull type pins are typically made with a solid or hollow shank containing a detent assembly in the form of a locking lug, button or ball which is backed up by a resilient core, spring or plug, and employed to fasten parts under shear loading. Ideally, the load direction is at right angles to the shank of the pin. Locking mechanisms are designed to provide secure retention against accidental disassembly and assembly.

Positive-locking pins that is usually independent of insertion and removal forces. These pins are also primarily suited for shear-load applications, although some tension loading can be tolerated without affecting pin function. Single-acting pins have locking action controlled by a plunger-actuated locking mechanism. In the locked position, the locking element projects beyond the surface of the pin shank to provide a positive lock. When the plunger is mover by means of a button or lever assembly at one end of the pin, the locking element retracts. A number of head styles and release mechanisms have been developed for these pins.

An example of such pins suitable for use with the present invention are quick release pins produced by Monroe quick release pins manufactured by Monroe PMP of Auburn Hills Mich., which are available in a variety of different styles and sizes to suit this intended application. Monroe offers styles including T-handle, L-handle, Button-handle and Ring-handle versions, and with different handle and button finishes as well as lanyards.

A pair of longitudinally rearwardly hand grips 262 and 264 are rigidly mounted to an upper portion of the sleeves 204 and 205, respectively, to assist the patient in mounting and dismounting the exercise device 10, as well as to assist in vertically repositioning the forearm pad 174.

Figure 4:
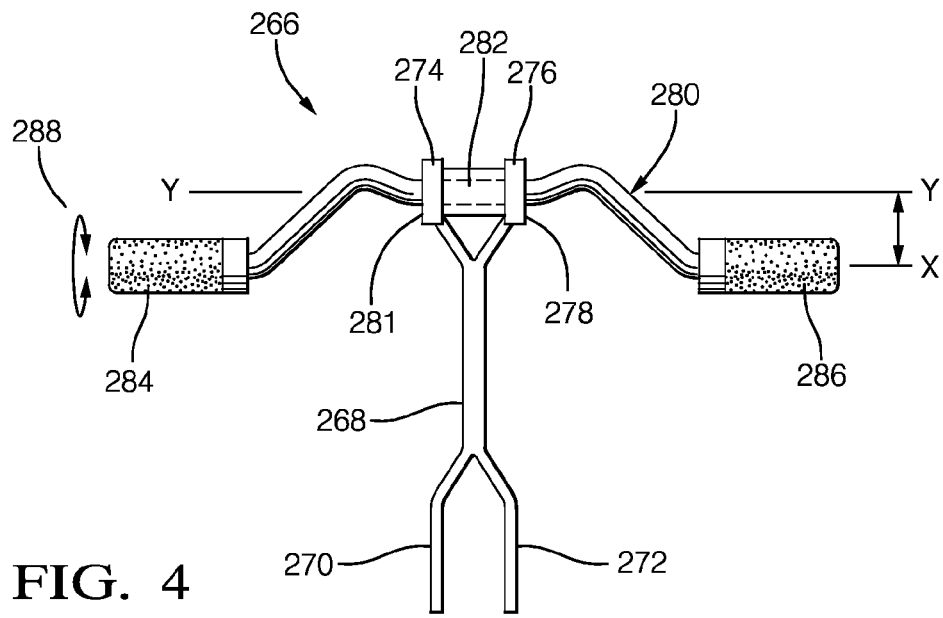
FIG. 4, is a side plan view of an alternative embodiment of a patient lifting device applicable with the muscular evaluation and exercise device of FIG. 1.

The straight handlebar 256 illustrated in FIG. 1 is known as a "wrist curl" type grip. Referring to FIG. 4, an alternative axially offset lever assembly 266 is illustrated, comprising an elongated beam 268 which is bifurcated at one end to form parallel flanges 270 and 272, and bifurcated at the opposite end to form a second set of parallel flanges 274 and 276. Flanges 270 and 272 are affixed to the elongate beam assembly 100 as described herein above. Flanges 274 and 276 are interconnected to the center portion 278 of a "bicycle type" grip through a rubber isolator 281 with a bronze bushing 282. The laterally opposed ends of the hand grip 280 are axially aligned (on axis "X") and include resilient grip members 284 and 286. The hand grip 280 is shaped such that the center portion of the grip 278 is on a lateral axis "Y" which is parallel to axis "X". In application, the entire grip 280 free to rotate about axis "Y" as illustrated by arrow 288. Simultaneously, the lever assembly 266 is free to rotate about an axis (not illustrated) formed by a quick release pin interconnecting the opposed flanges 270 and 272 to the elongate beam assembly 100 through a selected aperture 58. The resulting hybrid path of motion of the hands and upper arms of a patent employing the exercise device 10 is believed to provide significant therapeutic advantages.

Referring to FIG. 5, a top view of the padded seat 40 illustrates a shaped longitudinally rearwardly extending recess 290 formed in the front edge 292 thereof. This feature enables an expanded range of operation of the exercise device 10 wherein the forearm pad support mechanism 172 can be located longitudinally rearwardly to a point approaching the seat support structure 34. This maximizes the upward freedom of travel of the elongate beam assembly 100 without interfering with the padded seat 40.

Figure 2:
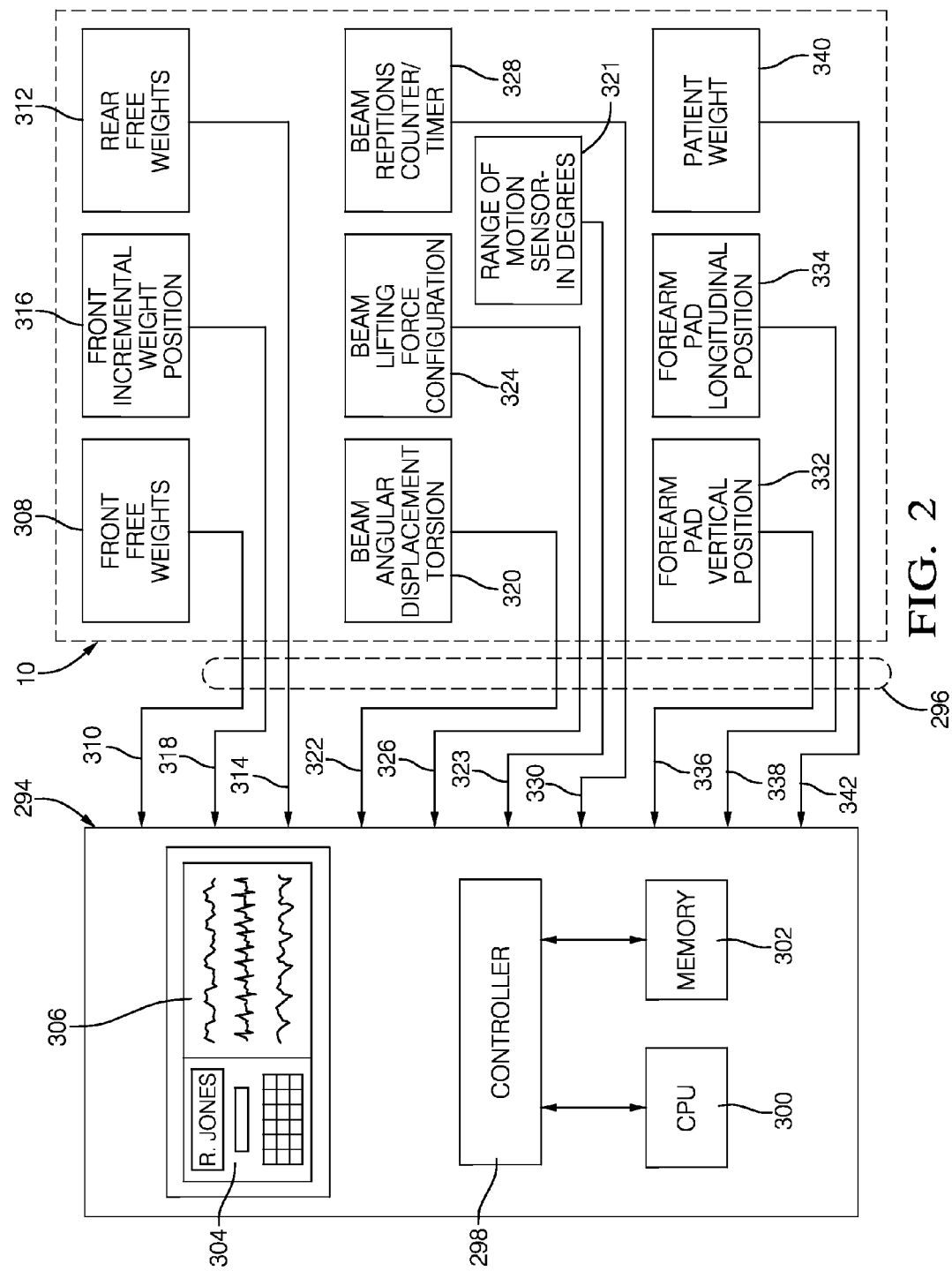
FIG. 2, is a simplified block diagram of a system controller and sensors incorporated within the muscular evaluation and exercise device of FIG. 1.

Referring to FIG. 2, the muscular evaluation and exercise device 10 embodying the present invention can be employed for routine home-based exercise. However, it is primarily intended for therapeutic applications in clinical settings. Exercise sessions as part of a therapy regimen require precise control of the patient's range of motion and the level of muscular exertion, as well as data record gathering, retention, processing and display for use by the clinician. Accordingly, the exercise device 10 can be instrumented with a suite of sensors and actuators which are interfaced with a dedicated data processor 294 through an umbilical connection 296.

Data processor 294 includes a controller circuit 298 interfaced with a central processor unit (CPU) 300, a non-volatile memory device 302, and clinician and/or user accessible inputs 304 and readouts 306 in analog or digital form. Furthermore, the data processor 294 receives a plurality of inputs from various sensors and actuators embedded within the muscular evaluation and exercise device 10.

The aggregate or cumulative weight of free weights 64 carried on weight support pin 62 can be measured by a weight sensor 308 disposed at the base of the support pin 62 and interconnected with the data processor 294 through a data or signal feed line 310. The weight sensor 308 can, by way of example comprise a pressure sensitive element such as a variable resistance pad or a fluid filled bladder located on the upper surface of the blade portion 56 of the elongate beam 42 upon which the stack of free weights 64 rests. The weight sensor 308 provides a continuous signal to the data processor 294 indicating the instantaneous weight borne on the front end portion of the elongate beam 42.

Similarly, the aggregate or cumulative weight of free weights 88 carried on weight support pin 86 can be measured by a weight sensor 312 disposed at the base of the support pin 86 and interconnected with the data processor 294 through a data or signal feed line 314. The weight sensor 312 can, by way of example comprise a pressure sensitive element such as a variable resistance pad or a fluid filled bladder located on the upper surface of the arcuate aft portion 84 of the counterweight beam assembly 78 upon which the stack of free weights 88 rests. The weight sensor 312 provides a continuous signal to the data processor 294 indicating the instantaneous weight borne on the rear end portion of the elongate beam 42.

The position of the tubular weight 68 along the axis of threaded shaft 70 can be monitored by a linear position sensor 316 such as a non-contacting type including a permanent magnet embedded within the tubular weight 68 for axial movement therewith, and a stationary linear Hall-effect device mounted on the blade portion 56 intermediate extensions 72 and 74. The linear position sensor 316 is and interconnected with the data processor 294 through a data or signal feed line 318.

With the three above-described data or signal inputs, the data processor 294 can calculate the positive moment arm provided by the fore end portion of the elongate beam 42, including fixed weights 64, forward of the rotational axis of the pivot assembly 52, the offsetting negative moment arm provided by the aft end portion of the elongate beam 42, including fixed weights 88, rearward of the rotational axis of the pivot assembly 52, and the incremental positive moment arm provided by the adjustable weight assembly 66. The controller 298 of the data processor 294 can then logically sum the three moment arm inputs and provide an aggregate summation thereof, as well as a determination of the total mass of the elongate beam assembly 100.

Rotary position sensors frequently employ a magnetic field and a galvanomagnetic sensing element, such as a Hall affect device or a magnetoresistor located within the magnetic field. To detect relative rotational movement between a first article (such as the rotatable elongate beam 42) and a second article (such as the stationary seat support structure 34), the magnetic field is oriented transverse in relation to the axis of rotation of the first article, and the galvanomagnetic sensing element is located inside the magnetic field. The member providing the magnetic field is connected to one of the articles, and the galvanomagnetic sensing element is connected to the other article. As the articles rotate relative to each other, the galvanomagnetic sensing element is caused to change its angular position relative to the magnetic field direction, resulting in a change of output signal from the galvanomagnetic sensing element responsive to its angle with respect to the magnetic field direction. This change in signal is indicative of the angular position as between the first and second articles.

An angular beam position sensor 320 is integrally formed within the pivot assembly 52 to bi-directionally sense user induced angular displacement of the elongate beam assembly 100. A signal feed line 322 provides output data to the data processor 294, which calculates directionality, user applied torsion, (de)acceleration, instantaneous position of the elongate beam 42. A related range of motion sensor 321 is configured to measure movement of the operator, measured in degrees. A signal feed line 323 provides output data to the data processor 294.

A combined tension/compression and angular position sensor 324 is integrated within the quick release pin 260 securing the user lifting lever 248 to the elongate beam 42, to output signals to the data processor 294 via a signal feed line 326. This provides a direct objective measure of instantaneous operator effort in displacing the elongate beam assembly between its end limits of travel.

A beam cycle repetition counter/timer 328 counts cycles and times the operator workout duration for recording and processing by the data processor 294 via a signal feed line 330.

A forearm pad vertical position sensor 332 and a forearm pad longitudinal position sensor 334, interconnected with the data processor 294 via separate data feed lines 336 and 338, respectively, provide user physiological data to the processor 294 and ensures continuity and consistency between workout sessions.

A pressure sensitive element 340 such as a variable resistance pad or a fluid filled bladder is incorporated within the padded seat 40 to monitor the weight of the operator and to provide related data to the data processor 294 via a signal feed line 342

There has been described herein above an exercise device for selectively developing the muscles of the user's upper body including the user's arms, back, wrists and shoulders. The device provides adjustment of the height of the forearm pad support and the lifting means, in the forward or rearward position of the forearm pad, forearm pad support and the lifting means, and in the radial position of the forearm pad.

It is to be understood that the invention has been described with reference to specific embodiments and variations to provide the features and advantages previously described and that the embodiments are susceptible of modification as will be apparent to those skilled in the art.

Furthermore, it is contemplated that many alternative, common inexpensive materials can be employed to construct the basis constituent components. Accordingly, the forgoing is not to be construed in a limiting sense.

The invention has been described in an illustrative manner, and it is to be understood that the terminology, which has been used is intended to be in the nature of words of description rather than of limitation.

Obviously, many modifications and variations of the present invention are possible in light of the above teachings. For example, the infinitely adjustable weight assembly 66, or a similar device(s) can be carried on the handle portion 54 to ensure displacement of tubular weight 68 through an axis extending through pivot assembly 52. Additionally, a range of motion indicator scale, similar to scale 113, can be carried on a side wall portion of the elongate beam 42 adjacent the adjustable weight to ensure repeatable precise positioning of the tubular weight. It is, therefore, to be understood that within the scope of the appended claims, wherein reference numerals are merely for illustrative purposes and convenience and are not in any way limiting, the invention, which is defined by the following claims as interpreted according to the principles of patent law, including the Doctrine of Equivalents, may be practiced otherwise than is specifically described.

The invention claimed is:

1. An exercise device for therapeutic development of targeted user musculature, said device comprising:
    a base;
    a seat supported above the base by a vertically extending structure;
    a forearm pad adjustably disposed forward of the seat and supported above the base by an adjustable forearm pad support;
    an adjustably counterbalanced beam assembly interconnected with said vertical seat structure by a pivot having a fixed axis enabling limited relative rotational freedom between a first and a second limit of travel, said counterbalanced beam assembly having an elongated fore end portion extending forwardly of said seat structure and adapted for supporting free weights for displacement therewith, and an arcuate aft end portion forming a substantially constant radius with respect to said pivot axis extending rearwardly through a longitudinal opening formed in said seat structure and adapted for supporting free weights for displacement therewith; and
    a lifting lever assembly pivotally attached to said fore end portion forward of said forearm pad.

2. The exercise device of claim 1, wherein said arcuate aft end portion of said elongate beam comprises a semi-circular member depending from said fore end portion adjacent said pivot, said semi-circular member having a substantially constant radius coaxially centered with said pivot.

3. The exercise device of claim 2, wherein said semi-circular member extends rearwardly through a registering slot formed in said seat support structure.

4. The exercise device of claim 3, wherein said semi-circular member carries a semi-circular scale registering with a fixed indicator carried by said seat support structure to provide an angular position indication to an attendant clinician.

5. The exercise device of claim 3, wherein said semi-circular member carries an intermediate stop operative to redefine said first or second limit of travel.

6. The exercise device of claim 1, further comprising an adjustable weight assembly carried on a threaded shaft with said fore end portion.

7. The exercise device of claim 6, wherein said adjustable weight assembly comprises an elongated guide member extending generally parallel to an axis of said elongate beam and a dedicated weight carried with said guide member for incremental axial adjustment there-along, and wherein said free weight support pin and said adjustable weight assembly are generally axially equidistant from said pivot.

8. The exercise device of claim 7, further comprising a plurality of free weights configured for selective placement on one of said support pins, said free weights being incrementally sized between a minimum weight of X Kg. and a maximum weight of Y Kg., wherein said dedicated weight weighs approximately 0.5X Kg.

9. The exercise device of claim 1, further comprising a dynamic tension device operative to resist rotational displacement of said counterbalanced beam assembly between said limits of travel.

10. The exercise device of claim 9, wherein said dynamic tension device comprises a fixed caliper operable to selectively engage opposed lateral surfaces of said counterbalanced beam assembly.

11. The exercise device of claim 10, wherein said caliper comprises an opposed pair of rollers positioned to simultaneously bear against said lateral surfaces.

12. The exercise device of claim 1, wherein said beam assembly comprises first free weight retention means carried with said fore end portion and second free weight retention means carried with said arcuate aft end portion, said first and second free weight retention means interposed by said pivot.

13. The exercise device of claim 12, wherein said first and second free weight retention means comprise upwardly extending support pins.

14. The exercise device of claim 1, wherein said fore end portion comprises a pivot assembly at one end thereof and an angularly offset extension member at an opposite end thereof, said extension member supporting an upwardly directed free weight support pin and a downwardly directed beam stop configured to abut said base when said counterbalanced beam is in said first limit of travel.

15. The exercise device of claim 1, wherein said beam assembly comprises a single rigid member extending between said fore and arcuate aft ends.

16. The exercise device of claim 1, wherein said seat and said forearm pad are independently vertically adjustable with respect to said base.

17. The exercise device of claim 1, further comprising lock means selectively operable to fixedly engage said beam assembly in any of a plurality of relative positions between said first and second limits of travel.

18. The exercise device of claim 1, further comprising an adjustable range limiting stop operable to establish said variable second limit of travel.

19. The exercise device of claim 1, wherein said lifting means comprises a generally tubular elongated handle bar forming axially aligned opposed hand hold portions and a central mounting portion disposed axially parallel with and offset radially from said hand hold portions.

20. An exercise device for therapeutic development of targeted user musculature, said device comprising:
- a longitudinally elongated base;
- a seat supported above the base by a vertically elongated tubular member;
- a forearm pad disposed longitudinally forward of the seat and supported above the base by a vertically and longitudinally adjustable forearm pad mechanism;
- an elongated fore beam having a first end portion interconnected to said vertically elongated tubular member by a pivot assembly disposed vertically intermediate said base and seat, said elongated fore beam extending forwardly of said forearm pad and terminating in a second end portion, said second end portion forming a rotational down-stop, a free weight support pin and an adjustable weight assembly;
- an arcuate aft counterweight beam supported by and extending longitudinally rearwardly from said elongated fore beam, said aft counterweight beam extending through a longitudinal opening formed in said vertically elongated tubular member and terminating in a free end forming a second free weight support pin, said arcuate aft counterweight beam formed in a constant radius about an axis defined by said pivot assembly,
- wherein said fore and aft free weight support pins can be selectively differentially loaded with free weights for rotational displacement therewith to vary total rotating system mass as well as weight imbalance;
- at least one repositionable stop member carried with said arcuate aft counterweight beam configured for engagement with an opposed outer surface of said vertically elongated tubular member to define a rotational up and/or down stop for said fore beam;
- a dynamic tension device carried within said vertically elongated tubular member and operable to selectively engage said arcuate aft counterweight beam; and
- a lifting lever assembly pivotally attached to said fore beam longitudinally forward of said forearm pad.

* * * * *